United States Patent
Wagner et al.

(10) Patent No.: US 8,425,812 B2
(45) Date of Patent: Apr. 23, 2013

(54) DENTAL BLANK AND METHOD OF MAKING A DENTAL CERAMIC BLANK

(75) Inventors: Ingo W. Wagner, Wörthsee (DE); Martin Goetzinger, Eching a. Ammersee (DE); Thomas Sprengart, Seefeld-Hechendorf (DE)

(73) Assignee: 3M Innovative Properties Company, Saint Paul, MN (US)

( * ) Notice: Subject to any disclaimer, the term of this patent is extended or adjusted under 35 U.S.C. 154(b) by 317 days.

(21) Appl. No.: 12/682,115

(22) PCT Filed: Oct. 10, 2008

(86) PCT No.: PCT/US2008/079479
§ 371 (c)(1),
(2), (4) Date: Apr. 8, 2010

(87) PCT Pub. No.: WO2009/049127
PCT Pub. Date: Apr. 16, 2009

(65) Prior Publication Data
US 2010/0209876 A1     Aug. 19, 2010

(30) Foreign Application Priority Data
Oct. 11, 2007   (GB) ................................. 0719824.5

(51) Int. Cl.
*A61C 13/20* (2006.01)
(52) U.S. Cl.
USPC ............................................. 264/16; 264/120
(58) Field of Classification Search ......................... None
See application file for complete search history.

(56) References Cited

U.S. PATENT DOCUMENTS

| | | | |
|---|---|---|---|
| 549,274 A * | 11/1895 | Mellen | 425/354 |
| 1,796,470 A | 3/1931 | Meyer | |
| 1,899,718 A | 2/1933 | Poston | |
| 2,355,853 A | 8/1944 | Foxon | |
| 2,409,783 A | 10/1946 | Moskey | |
| 2,883,703 A * | 4/1959 | Frank | 425/78 |
| 3,276,122 A | 10/1966 | Slayton | |
| 3,495,333 A | 2/1970 | Kuhn | |
| 3,664,785 A * | 5/1972 | Marshall et al. | 425/78 |
| D278,744 S | 5/1985 | Miener | |

(Continued)

FOREIGN PATENT DOCUMENTS

| | | |
|---|---|---|
| CA | 2280352 | 2/2000 |
| DE | 29815486 | 2/2000 |

(Continued)

OTHER PUBLICATIONS

Product Literature: 3M ESPE, "Lava®, Der Rohstoff für perfekte Vollkeramik", Scientific Affairs, 6 pgs., Mar. 2001.

(Continued)

*Primary Examiner* — Mary F Theisen
(74) *Attorney, Agent, or Firm* — Carlos M. Téllez; 3M Innovative Properties Company

(57) ABSTRACT

A method of making a dental blank comprises the steps of independently compacting a first and second zone of a quantity of ceramic particles. During compacting, the first and second zones have different compaction factors in at least one stage. Such blanks may be pre-sintered and used in the manufacture of dental restorations. The method may help in controlling the homogeneity of the material structure during manufacturing the blanks.

14 Claims, 5 Drawing Sheets

U.S. PATENT DOCUMENTS

| | | | | |
|---|---|---|---|---|
| 4,536,366 A | * | 8/1985 | Inoue | 419/11 |
| 4,615,678 A | | 10/1986 | Moermann | |
| D297,762 S | | 9/1988 | Ito | |
| 5,043,123 A | * | 8/1991 | Gormanns et al. | 264/113 |
| 5,135,393 A | | 8/1992 | Eidenbenz | |
| 5,160,747 A | * | 11/1992 | Kizaki et al. | 425/352 |
| 5,259,744 A | * | 11/1993 | Take | 425/78 |
| 5,306,673 A | | 4/1994 | Hermansson | |
| 5,378,416 A | * | 1/1995 | Kishi et al. | 264/40.5 |
| 5,383,752 A | | 1/1995 | Rheinberger | |
| 5,490,810 A | | 2/1996 | Hahn | |
| 5,551,856 A | * | 9/1996 | Katagiri | 425/78 |
| 5,632,941 A | * | 5/1997 | Mehrotra et al. | 264/656 |
| 5,647,704 A | | 7/1997 | Turchan | |
| 5,698,149 A | * | 12/1997 | Hinzmann et al. | 264/120 |
| 5,813,859 A | | 9/1998 | Hajjar | |
| 5,849,068 A | | 12/1998 | Hofmann | |
| 6,074,584 A | * | 6/2000 | Hinzpeter et al. | 264/40.5 |
| 6,099,772 A | * | 8/2000 | Hinzmann et al. | 264/109 |
| 6,113,378 A | * | 9/2000 | Tsuboi et al. | 425/352 |
| 6,190,171 B1 | | 2/2001 | Hajjar | |
| 6,224,371 B1 | | 5/2001 | Deluca | |
| 6,454,568 B1 | | 9/2002 | Beuschel | |
| 6,641,340 B1 | | 11/2003 | Hajjar | |
| 6,769,912 B2 | | 8/2004 | Beuschel | |
| 6,905,293 B1 | | 6/2005 | Filser | |
| 7,077,391 B2 | | 7/2006 | Filser | |
| D627,472 S | | 11/2010 | Wagner | |
| D627,473 S | | 11/2010 | Wagner | |
| D627,889 S | | 11/2010 | Wagner | |
| 2003/0031984 A1 | | 2/2003 | Rusin | |
| 2003/0132539 A1 | | 7/2003 | Althoff | |
| 2004/0072121 A1 | | 4/2004 | Filser | |
| 2004/0168610 A1 | | 9/2004 | Conrad | |
| 2010/0000677 A1 | | 1/2010 | Guggenmos | |

FOREIGN PATENT DOCUMENTS

| | | |
|---|---|---|
| DE | 4436231 | 1/2006 |
| EM | 1018766-1/3 | 11/2008 |
| EP | 0391446 | 10/1990 |
| EP | 0455854 | 11/1991 |
| EP | 0480238 | 4/1992 |
| EP | 0759728 | 11/1995 |
| EP | 0807422 | 11/1997 |
| EP | 0982009 B1 | 3/2000 |
| JP | 10192305 | 7/1998 |
| JP | 2000-107202 | 4/2000 |
| WO | WO 95/30382 | 11/1995 |
| WO | WO 01/97707 | 12/2001 |
| WO | WO 0245614 | 6/2002 |
| WO | WO 2007/141324 | 12/2007 |
| WO | WO 2008/000313 | 1/2008 |

OTHER PUBLICATIONS

Product Literature: 3M ESPE, "Lava™ CAD/CAM System für vollkeramische Restaurationen", 2 pgs., May 2002.

Product Literature: 3M ESPE, Nbr. 70200948852 / 01 (Apr. 2002), "Lava™ CAD/CAM System für vollkeramische Restaurationen", 8 pgs., Apr. 2002.

Product Literature: 3M ESPE, Products 2003/2004, Catalog pp. 98-99.

Product Literature: ESPE Dental AG, "LAVA Prozesskette", 1 pg., (date unknown but believed to be earlier than the effective US filed and any foreign priority date).

Product Literature: HintElis DentaCAD Systeme, "Hint-Els® virus", 4 pgs., Apr. 15, 2005.

Product Literature: HintEls DentaCAD Systems, "Trade Fair Offerings", 2 pgs., Mar. 21, 2007.

Product Literature: IPS e.max, "all ceramic all you need", 4 pgs., Mar. 2007.

Product Literature: KaVo Dental GmbH, "Reaching the peak of CAD/CAM performance", 4 pgs., Mar. 21, 2007.

Product Literature: Kavo, "Kavo Everest® CAD/CAMSystem, Mit Materialvielfalt an die Spitze.", 12 pgs., (date unknown but believed to be earlier than the effective US filing date and any foreign priority date).

Product Literature: Kavo, Nbr. 1003.8925 / 111/05, "Kavo Everest® Zirkonkeramik. Für exzellenten Zahnersatz", 10 pgs., Apr. 15, 2005.

Product Literature: Schütz Dental GmbH, "Tizian™ CAD/CAM, Zirkon ohme Limit", Mandler, 3 pgs, Mar. 2007.

Product Literature: Schütz Dental GmbH, "Tizian™ Mill", Mandler, 5 pgs, Mar. 2007.

Product Literature: Sirona, Dispo-Nr. 04605, 201305C6026 WS 03078, "Mit inLab ist Erfolg immer ausbaufähig", 4 pgs., Mar. 21, 2002.

Product Literature: Von Ekton, "CAD/CAM von etkon— Die Zahntechnik ist am Ziel.", 6 pgs., Apr. 15, 2005.

Product Literature: Wieland Dental Division, Nbr. 530075d.00.02. 07, "Das Zeno® Tec System", 16 pgs., Feb. 2007.

Product Literature: Zirkon Zahn, "The Original", 14 pgs., Mar. 2007.

Search Report for GB 0719824-5, 1 pg.

Search Report of International Application No. PCT/US2008079479, 5 pgs., Jun. 12, 2009.

User Newsletter: DeGuDent GmbH, "Cercon Smart Ceramics", vol. 1, 6 pgs., (2004).

Written Opinion of International Application No. PCT/US2008079479, 9 pgs., Oct. 11, 2007.

* cited by examiner

Single Zone Compression

Single Zone Compression

DENTAL BLANK AND METHOD OF MAKING A DENTAL CERAMIC BLANK

CROSS REFERENCE TO RELATED APPLICATIONS

This application is a national stage filing under 35 U.S.C. 371 of PCT/US2008/079479, filed Oct. 10, 2008, which claims priority to GB Application No. 0719824.5, filed Oct. 11, 2007, the disclosure of which is incorporated by reference in its/their entirety herein.

FIELD OF INVENTION

The invention relates to a method for making a dental blank of a ceramic material, including compacting the ceramic material. Further, the invention relates to a blank of a ceramic material and a use of the blank.

BACKGROUND OF THE INVENTION

Dental restorations or prostheses are often made of ceramic materials because ceramic materials generally provide relatively good physical, aesthetic and biological properties. These restorations are often manufactured by an automated process, which typically includes:
- capturing data representing the shape of a patient's teeth, for example by scanning a plaster model of the patient's teeth or alternatively by scanning the actual teeth in the patient's mouth;
- designing the shape of a dental restoration precursor based on the captured data using software, such as computer-aided design (CAD) software;
- machining the dental restoration precursor to correspond to the designed shape, for example, by an automated Computer Numerical Controlled (CNC) machine; and
- optionally finishing the dental restoration precursor by sintering and/or veneering.

A common method of making dental restorations includes milling a restoration precursor out of a blank of a pre-sintered but still porous ceramic material. The blank is typically formed by compacting an amount of ceramic powder. The blank of compacted powder is usually subsequently pre-sintered to provide it with the required mechanical stability for handling and machining. Once the restoration precursor has been obtained from machining the blank the precursor is typically sintered in the further process of making the final dental restoration. During sintering the precursor typically shrinks, generally proportionally, because the initially porous material reduces in porosity and increases in density. For this reason the restoration precursor may be initially larger, for example about 20 to 30%, than the desired final shape after sintering, to account for shrinkage during the sintering step. To form the final dental restoration the sintered restoration precursor may be veneered or otherwise finished.

It has been found desirable that the material structure of the blank is of a generally uniform density. This is because a non-uniform density or inhomogeneity of the blank material may cause the raw dental restoration to shrink non-uniformly in one or more dimensions during sintering. Thus, the precision of the final dental restoration may be adversely affected, resulting in wasted time and expense for a dentist.

It is generally difficult to compact the ceramic powder to create a blank having a generally uniform or homogeneous material structure. Typically compacting the powder requires the powder particles to move relative to each other. However, thereby friction may hinder the movement of the particles. This may result in the particles to block regionally, and such regions may sink again during further compaction while other regions block, and so on. Therefore the blank may have regionally different densities, or in other words the blank may have to some extent an inhomogeneous material structure.

Isostatic compacting processes are often used to manufacture blanks with a relatively homogeneous inner structure. Isostatic compacting processes typically are based on the use of liquid to apply pressure to the ceramic material generally uniformly from all sides, or isotropically. Typically the isostatic processes are used with cylindrical blanks because the cylindrical shape provides for relatively isotropic compaction, and therefore provides for a relatively homogeneous inner structure of such blanks. However, there have been efforts to find alternative compacting techniques that are less expensive, and/or which can be reliably used for different blank shapes.

It is further still desired to manufacture non-cylindrical blanks with a consistently high degree of homogeneity of the inner material. Also, it is a general desire to provide a relatively inexpensive manufacturing process. Especially for dental purposes there is also demand for a manufacturing process that provides for maintaining a high hygiene level during production.

SUMMARY OF THE INVENTION

In a first aspect the invention is concerned with a method of making a dental blank from a quantity of ceramic particles. The method comprises the steps of:
- compacting a first zone of the quantity of ceramic particles;
- compacting a second zone of the quantity of ceramic particles;
- wherein the first and second zones have different compaction factors in at least one stage (or at least one point in time) during compacting the first and second zones, and wherein the compaction of the first and second zones can be independently controlled.

The invention may provide for a relatively homogeneous inner structure of the blank. In particular, the blank may have a relatively large portion of relatively homogenously compressed material. The invention may further allow the use of uniaxial compressing techniques to make a dental blank at the required homogeneity level. Therefore the invention may also be relatively inexpensive, for example relative to isostatic compression techniques. Furthermore, the invention may allow for making blanks having non-cylindrical shapes. This may be advantageous in particular for making several restorations or one or more larger restorations, like a bridge, from one blank. For example, a blank having a generally cuboid shape typically provides for more effective use of the material (less waste) when used for making large restorations, such as bridges. This is because such restorations typically have an arc-like configuration which typically would require a cylindrical blank of a relatively large diameter so that the entire shape of the restoration would fit within the volume of the blank. In contrast, an arc-like restoration would typically fit within a cuboid-shaped blank having a lower volume.

"Independently controlling the compaction of the first and second zones" may comprise application of a first physical action effective for increasing the density of the first zone of the quantity of ceramic particles, and the application of a second physical action effective for increasing the density of the second zone of the quantity of ceramic particles, wherein the first and second physical actions are different or applied according to different parameters. For example the first and second zones may be compacted at one or more of different compacting speeds;
different compacting forces; and
different compaction factors.

The term "compaction" preferably comprises the application of a physical action effective for increasing the density of a quantity of ceramic particles.

"Compaction factor" ($C_F$) is understood as the ratio of:
a first volume ($V_1$) of a quantity of particles,
to
a second volume ($V_2$) of the same quantity of particles at a compacted stage:

$$C_F = V_1/V_2$$

The ceramic particles preferably comprise or are comprised of a ceramic material. Although the specific ceramic particles and ceramic material selected are not believed to be critical to the performance of the present invention, in one embodiment the ceramic material may comprise between 90 and 99% by weight zirconium oxide, and preferably 91 to 97.25% by weight zirconium oxide. The ceramic material may further comprise 0-1% by weight aluminium oxide. The ceramic material may also be based on aluminium oxide, meaning the ceramic material may comprise 90 to 99% by weight aluminium oxide and 0 to 1% by weight zirconium oxide. Further, the ceramic material may comprise 0-10% by weight of at least one of hafnium oxide, yttrium oxide and oxides from gallium, germanium, and indium, as well as 0.0005 to 1.5% by weight of colouring additives, selected from the group consisting of the oxides $Fe_2O_3$, $Er_2O_3$ and/or $MnO_2$. The ceramic material is preferably selected to be compatible for use in human bodies.

The first and second zones of the quantity of the ceramic particles may be substantially separate, for example may not overlap substantially. Further, the first and second zones at a compacted stage may together form the blank. The first and second zones at a compacted stage may further form one continuous larger zone that forms the blank.

The compaction factor of the first zone ($C_{F, 1st zone}$) and the compaction factor of the second zone ($C_{F, 2nd zone}$) may be in a zone-to-zone compaction ratio ($C_{F, 1st zone}/C_{F, 2nd zone}$) of between 0.8 and 2.0, or may be in more particular in a ratio of between 0.5 and 1.2. The compaction factor of the first zone may in particular be greater than the compaction factor of the second zone.

The method of the invention in one embodiment includes providing the ceramic particles in a chamber of a compression tool. The compression tool may comprise a first and a second movable member that are adapted to close the chamber. Preferably the first and the second movable members in combination or co-operation are adapted to close the chamber. The first and second movable members are preferably movable independently from one another and preferably movable generally parallel or co-axially relative to one another. Further, the first and second movable members are preferably adapted to exert pressure on the ceramic particles that may be provided in the chamber. A ceramic material provided in the chamber may be compacted by moving the first and/or second movable members into the chamber. The pressure on the ceramic material may also be exerted otherwise, for example by hydraulic pressure or by any other suitable media or appliance.

In a particular embodiment, compacting the first zone is associated with moving a first movable member, and preferably compacting the second zone is associated with moving a second movable member. Preferably compacting the first and second zones includes moving the first and second movable members, respectively, independently from one another.

Further, compacting the first and second zones preferably includes moving the first and second movable members generally parallel to one another, and preferably in substantially the same direction. Compacting the first and second zones may also include moving the first and second movable members generally co-axially with one another, and preferably in substantially the same direction.

In at least one stage (or at least one point in time) during compacting the first and second zones, the first and second movable members are preferably moved relative to one another at a speed ratio of between 5:1 to 1:3, or in more particular in a speed ratio of between 5:6 to 2:3 and preferably at a speed ratio of about 3:4.

In a preferred embodiment of the invention the first movable member is in contact with the quantity of ceramic particles during compaction of the second zone, and the second movable member is in contact with the quantity of ceramic particles during compaction of the first zone.

The movement of the first and/or second movable members may be "position controlled" (meaning may be moved by controlling their position and accepting different forces), or may be "force controlled" (meaning may be moved by controlling the force and accepting different positions). Position and force control may also be combined, for example controlling the position and the force simultaneously, or controlling the position and force alternately.

Moving of the first and/or second movable members may comprise positioning each of the movable members at a predetermined position. Thereby the first and/or second movable members may be moved until a certain compaction factor is reached. The force that may be required to move the first and/or second movable members may thereby controlled as required. However the force may be monitored, and upon exceeding a maximum force that could result in damages of the tool and/or the machine movement may be stopped and an error may be indicated.

In another embodiment, moving of the first and/or second movable members may comprise positioning each of the movable members by controlling a force or forces used to move the first and/or second movable members. In this case, the first and/or second movable members may be moved until a certain force is reached. The movable members thereby typically reach their desired position when the force used to move the movable members reaches a pre-determined maximum force. However the position of the first and/or second movable members may be monitored, and upon detecting a position that could result in damages of the tool and/or the machine movement may be stopped and an error may be indicated.

The first and second movable members may shape first and second outer surfaces of the blank, respectively. Further, the first and second outer surfaces of the blank may form a generally continuous or planar outer blank surface, for example. In particular, the first and second outer surfaces of the blank may form first and second planes, respectively, that are generally co-planar. The first and second movable members may also shape first and second outer surfaces of the blank, respectively, which may be parallel and offset from one another. Thus, there may be a step between the first and second outer surfaces. For example, the first and second outer surfaces may be parallel offset planes, and the blank may include other outer surfaces.

In another embodiment of the invention the method further comprises compacting a third zone of the quantity of ceramic particles. Although the blank may have more than three zones, for clarity all zones in addition to the third zone are referred to collectively as "the third zone". The third zone and the second zone have preferably different compaction factors in at least one stage (or at least one point in time) during compacting the first, second and third zones. The third zone and the first zone may have generally equal compaction factors during compacting the first, second and third zones. The zone-to zone compaction ratio of the third and second zones are therefore preferably in ratio of between 0.8 and 2.0, or may be in more particular in a ratio of between 0.5 and 1.2.

The first, second and third zones at a compacted stage may together form the blank. The first and second zones at a compacted stage may further form one continuous larger zone that forms the blank.

Compacting the third zone may be associated with moving a third movable member for compacting the third zone. In case of the presence of more than three zones, such additional zones may be associated with moving additional members for compacting the respective additional zones. Compacting the third zone is preferably independent from compacting the second zone, and preferably associated with compacting the first zone. However, compacting the third zone may also be independent from compacting the first zone and from compacting the second zone. Furthermore compacting the first, second and third zones includes moving the first, second and third movable members in generally the same direction.

Accordingly the compression tool may have a third movable member, or additional movable members. The third movable member may be movable independently from the first and second movable members. The third movable member may also be coupled to the movement of the first movable member, or at least be moved generally synchronously with the first movable member. For example, the first, second and third movable members may be arranged side-by-side, with the second movable member being movable relative to the first and third movable members.

In another embodiment of the invention the compression tool comprises a plurality of movable members. The plurality of movable members may be movable independently from one another. For example, the movable members may be arranged in a two-dimensional matrix, for example side by side, and together form a compression stamp composed of individual movable members. The compression stamp may overall have a shape so that it can be moved into a chamber of the tool. The movable members located towards the center of the stamp may be driven at lower forces and movable members located more towards the margin of the stamp may be driven at higher forces. Therefore, the compression stamp may be adapted to compress outer areas of a quantity of ceramic particles, for example filled in the chamber, at higher forces than inner areas. This may help to compress the quantity of ceramic particles at a rather uniform homogeneity. The plurality of movable members may be movable individually or in groups at different force levels (may therefore be "force controlled"). The plurality of movable members may further be movable individually or in groups to certain positions (may therefore be "position controlled").

In another embodiment of the invention the method preferably further comprises the step of removing at least part of the first and/or third zone(s). The method may also comprise the step of substantially removing the first and/or third zone (s). For example, the blank may be made by the method of the invention so that the blank has first, second and, optionally, third zones, and the first and/or third zone(s) is/are removed in a subsequent step. The zone or zones that are removed are typically the outer zones, leaving one or more inner zones as the blank. This may be advantageous because it is generally difficult to compact a blank or body so that it obtains an overall homogeneous inner structure. The method of the invention may preferably provide for producing a blank having a relatively large defined continuous zone in which the ceramic particles are arranged in a relatively desirable structure, for example in which the ceramic particles are arranged uniformly. Further zones having a more undesirable structure may thereby be minimized, for example zones in which the ceramic particles are arranged more non-uniformly. Although in this particular embodiment the waste may not be minimized, the usable amount of the ceramic material may be maximized.

In a particular embodiment of the invention, compacting the first zone of the quantity of ceramic particles is associated with moving a first pair of preferably cooperative movable members, and compacting the second zone of the quantity of ceramic particles is preferably associated with moving a second pair of cooperative movable members. Accordingly, compacting the third zone of the quantity of ceramic particles (when used) may further be associated with moving a third pair of cooperative movable members. Preferably, in this embodiment each of the first, second and optionally the third pairs of movable members have an upper and a lower movable member with the respective upper and lower members being moved in opposite directions relative to one another.

The first zone may therefore be compacted between the first pair of movable members, and the second zone may be compacted between the second pair of movable members. Accordingly, the third zone may therefore be compacted between the third pair of movable members, and so on.

A second aspect of the invention is related to a blank of a quantity of compacted ceramic particles. The blank is preferably made by a method according to the invention. The blank has in a plane of a first dimension an overall rectangular first cross-section. A longitudinally-extending recess or groove may be positioned at least one edge of the first cross-section, which is otherwise generally rectangular. Therefore the first cross-section may be generally L-shaped. A blank manufactured with the recess it may have a different inner material structure compared to a blank without the recess. In particular, the material structure of the blank having the recess may be more uniform in a certain area from which a dental restoration may be produced.

In a particular embodiment the dental blank in a plane of a second dimension has an overall rectangular second cross-section. The second dimension is preferably generally perpendicular to the first dimension. Further, the dental blank in a plane of a third dimension may have an overall rectangular third cross-section, with the third dimension preferably being generally perpendicular to the second dimension. The third dimension is also preferably generally perpendicular to the first dimension. Therefore, the blank may be shaped generally cuboid with at least one edge of the cuboid being replaced by a longitudinally-extending recess or groove. The at least one edge may also be partially substituted by an individual recess, or partially substituted by two or more recesses.

In another embodiment of the invention, the first cross-section comprises two, three or four recesses each being positioned at an edge of the first cross-section. Further, any of the second and the third cross-sections of the dental blank may comprise one, two, three or four recesses each being positioned at an edge of the respective cross-section. Preferably the second and the third cross-sections are also otherwise (without the recesses) generally rectangular.

At least one recess extends preferably longitudinally along the blank. In particular, the at least one recess may longitudinally extend along the entire length of the blank. For example, the blank may have a general L-shaped (1 recess), a general T-shaped (2 recesses) or a general cross-shaped (4 recesses) cross-section extending over a certain length. Preferably the areas of the recesses are smaller than 10% of the area of the nominally rectangular cross-section the recesses are associated with. Such recesses may, in addition to helping influencing the inner structure of the blank, further provide for material savings relative to a blank having a rectangular shape without recesses. The recess(es) is/are preferably generally V-shaped or U-shaped. A U-shape also includes a generally or partially round or circular structure (without straight legs).

In a particular embodiment at least one of the recesses is adapted to receive a gripping member. Such gripping member may be shaped to engage with the recess. Further, the gripping member may allow for handling (for example lifting, positioning, guiding) of the blank. In another embodiment at least two recesses are adapted to cooperate for receiving a gripping member. For example the recesses may form a dove tail at the blank.

The blank which may be made according to an embodiment of the invention may have first and second zones as described above. At least one side wall of the blank may be formed by the first zone. The first zone may, for example, partially or generally entirely surround the second zone of the blank on several or all sides. A blank made according to another embodiment of the invention may have a first, second and a third zone. Opposite outer side walls of the blank may be formed by the first and third zones with the second zone located between. A circumferential side wall of the blank may further be formed by a first zone that circumferentially surrounds the second zone.

In a further embodiment of the invention the blank has preferably a material density of between 44% and 56% of the theoretical density of the quantity of ceramic particles prior to compaction, in particular between 46% and 54%, and in more particular between 47% and 52% of the theoretical density of the quantity of the ceramic particles prior to compaction.

A fourth aspect of the invention is related to a use of a dental blank according to the invention for making a dental restoration. The making of the dental restoration preferably involves milling and/or grinding. The dental blank may, for example, be milled and/or ground to create a precursor of a crown, bridge, inlay or onlay or any other dental restoration or part thereof. That precursor may be sintered afterwards to form the dental restoration or a framework for a dental restoration. The framework is typically subsequently coated or provided with a veneer. In that case the veneer typically provides the dental restoration with a pleasant appearance, and the framework provides the dental restoration with good mechanical properties. It is also possible to make the veneer according to the embodiments as described herein. For example the blank may be milled and/or ground to form a veneer precursor (or part of it) and the veneer precursor may be sintered to form the veneer. The veneer may further be provided with gloss and/or it may be polished.

DETAILED DESCRIPTION OF THE DRAWINGS

In the following first a compression technique and tool are described using only one compression die (or only two opposing compression dies) for making a blank (further referred to as "single-zone compression"). And based on this, secondly the invention is explained by example of a compression technique and tool that use more than one (or more than two opposing) compression dies, further referred to as "multi-zone compression". Multi-zone compression is believed to influence the movement of the ceramic particles relative to one another during the compacting process. Therefore making a blank by multi-zone compression rather than single-zone compression may allow for better control of the blank material structure. In particular, multi-zone compression may provide for creating a blank having a rather large relatively homogeneous material density.

Figures 1, 2:
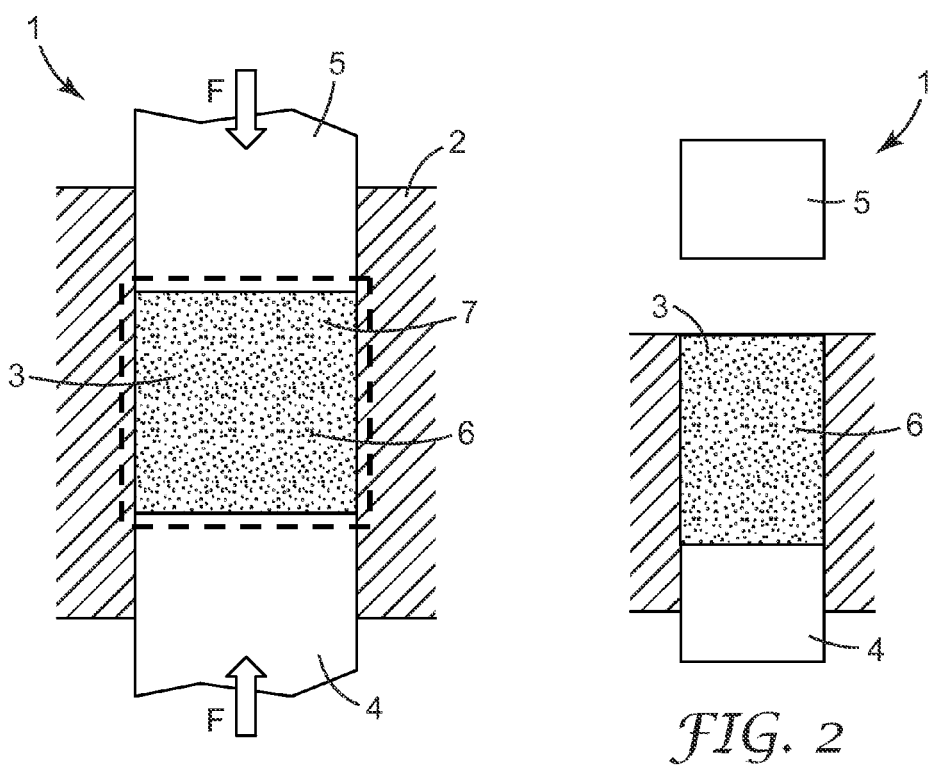
FIG. 1 is a schematic cross-sectional view of a tool for compacting ceramic particles.
FIG. 2 is another schematic cross-sectional view illustrating the use of the tool of FIG. 1.

FIG. 1 schematically shows a tool 1 for making a dental ceramic blank as it may be used for compacting ceramic particles, which may be provided in powder form. The tool comprises a support 2 forming a through-hole 3 in which compression dies 4, 5 are arranged on opposite sides. The example of FIG. 1 shows a tool as it is particularly used for preparing blanks of a generally cuboid shape. Therefore the support 2 is typically a frame forming a through-hole 3 having a generally rectangular cross-section, and the opposing surfaces of the compression dies 4, 5 are generally parallel to one another. The support 2 and the compression dies 4, 5 form a closed chamber 7 in which the ceramic particles 6 are placed. Each of the compression dies 4, 5 are moveable within the through-hole 3 towards and away from the other compression die. In particular there is a lower compression die 4 and an upper compression die 5. The terms "upper" and "lower" as they are used to designate the compression dies of the examples are used for ease of explanation only. The compression dies may instead be arranged at any angle or orientation. For filling the chamber 7 with a quantity of ceramic particles the lower compression die 4 is typically placed in the through-hole 3, so that the through-hole 3 is closed at the lower side, creating a chamber with the support. The upper compression die 5 is located outside the through-hole 3 (FIG. 2) so that the through-hole 3 is open at the upper side. Thus, the lower compression die 4 and the support 2 form a chamber that is open at the upper end for receiving the ceramic particles 6. After insertion of a predefined quantity of ceramic particles the upper compression die 5 is moved into the chamber and forms the closed chamber 7 in FIG. 1.

The dental ceramic blank is then made by compacting the ceramic particles 6. This is typically done by moving at least one of the lower compression die 4 and the upper compression die 5 towards the other. Typically a compression force F is applied to one or both of the compression dies 4, 5. Therefore the compression dies 4, 5 typically move towards one another until a certain maximum compression force is reached so that the ceramic particles are compacted to a certain predetermined density. The compression dies 4, 5 may also be controlled to move towards one another until a certain position is reached so that the ceramic particles are compacted to a certain predetermined volume. The compression dies 4, 5 may be held in position for a certain time period before they are moved away from one another again, so that the finished blank can be removed from the tool 1.

It is typically assumed that the quantity of ceramic particles is compacted to the desired extent when it has been compressed by controlling the compression dies 4, 5 at a certain compression force or to a certain position for a certain time period. However, the compaction level and the homogeneity of the compacted quantity of ceramic particles typically depend on the friction between the ceramic particles and between the particles and the tool, in particular between the ceramic particles and the walls of the through-hole 3. Such friction further typically hampers the homogeneous compaction of the ceramic particles. This means that a blank that is compacted in a tool as shown in FIGS. 1 and 2 typically has different inner areas of a different material density, which may exist in the prior art.

Figure 3:
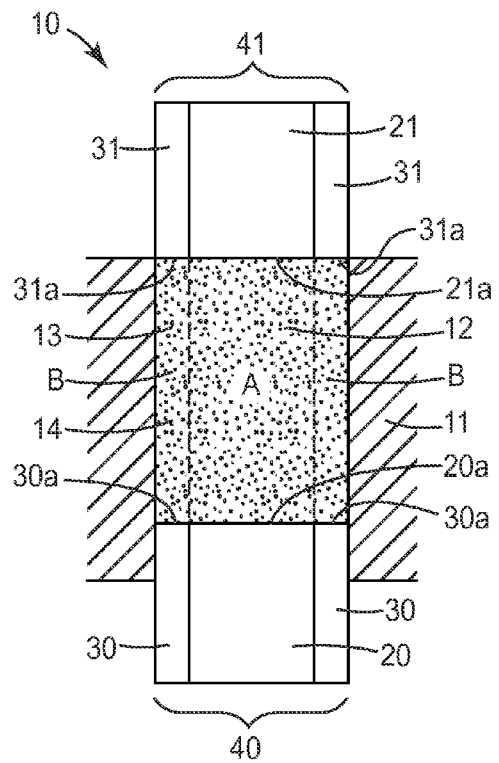
FIG. 3 is a schematic cross-sectional view of a tool containing a generally non-compacted ceramic particles according to an embodiment of the invention.

In FIG. 3 a tool 10 according to the invention is shown. The tool 10 has a support 11, outer and inner compression dies 30, 20 that form a compression die arrangement 40, and outer and inner compression dies 31, 21 that form a compression die arrangement 41. The compression die arrangements 40, 41 are movably received in a through-hole 13 of the support 11 on opposite sides. The support 11 with the through-hole 13 and the compression die arrangement 40 forms a chamber in which a quantity of ceramic particles is filled.

The outer compression dies 30, 31 in this example are frames that surround the inner compression dies 20, 21, respectively. The outer and inner compression dies 30, 20 as well as outer and inner compression dies 31, 21 are movable relative to one another. Thus the compression die arrangements 40, 41 with the support 11 form a closed chamber 12. The fit between the compression dies and/or the compression dies and the support preferably leaves sufficient space to permit air to escape during compression of the ceramic particles.

Figure 4:
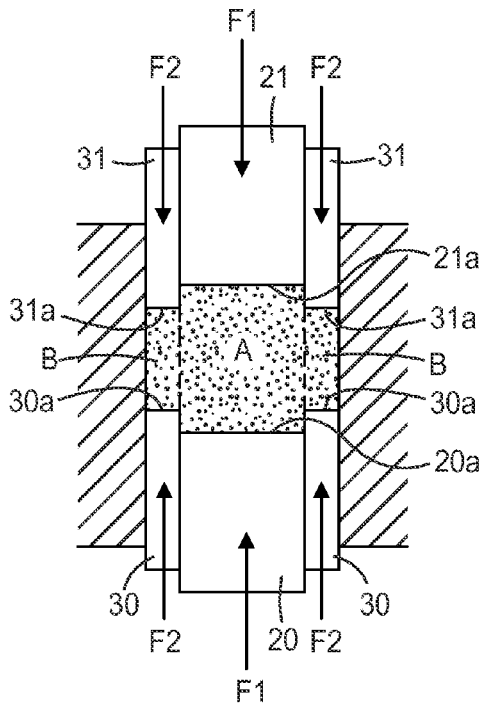
FIG. 4 is a schematic cross-sectional view of a tool containing a more compacted ceramic particles according to an embodiment of the invention.

The outer compression dies 30, 31 are independently movable from the inner compression dies 20, 21 as indicated in FIG. 4. Thus, the outer compression dies 30, 31 and the inner compression dies 20, 21 are movable relative to one another.

The example illustrated in FIGS. 3 and 4 shows the ceramic particles in a non-compacted state (FIG. 3) and in a compacted state (FIG. 4). In FIG. 3 the ceramic particles are substantially evenly distributed within the chamber. This may be achieved due to naturally good free-flowing capabilities of the ceramic particles so that a rather uniform distribution of the particles may be provided automatically after the particles have been filled in the chamber. However, a uniform distribution of the particles may also be obtained by exposing the ceramic particles to mechanical vibration, for example, after they have been filled in the chamber. In FIG. 4 relative to FIG. 3 the compression arrangements 40, 41 are positioned closer towards one another. Further, the outer compression dies 30 and 31 are displaced relative to the inner compression dies.

As shown in FIG. 3 the compression dies 20, 21, 30, 31 have compression surfaces 20*a*, 21*a*, 30*a*, 31*a* respectively. The compression surfaces 20*a*, 21*a*, 30*a*, 31*a* are in contact with the ceramic particles during the material is compacted. In FIG. 3 the upper inner and outer compression surfaces 21*a*, 31*a* are shown in a co-planar position with one another, as well as the lower inner and outer compression surfaces 20*a*, 30*a*. In contrast, in FIG. 4 the upper inner and outer compression surfaces 21*a*, 31*a* are offset relative to each another, and also the lower inner and outer compression surfaces 20*a*, 30*a* are offset relative to each another. The inner and outer pressing dies may also exert different forces F1, F2 to the zones A and B respectively, and/or move to different positions. In the example of FIG. 4 the inner compression surfaces 20*a*, 21*a* are offset behind the outer compression surfaces 30*a*, 31*a* respectively, however, a variety of other situations are possible. For example the inner and outer compression surfaces may be offset inversely, meaning with the inner compression surfaces projecting relative to the outer compression surfaces. Further, the upper or lower compression surfaces may be generally co-planar, and the respective other compression surfaces may be offset from one another. Other configurations are also possible, for example more than two upper and/or lower compression dies may be used that may be positioned at any appropriate position (with some or all dies being co-planar or offset relative to one another) for compacting the ceramic particles.

The chamber 12 contains ceramic particles 14. The ceramic particles in the chamber 12 may be divided in imaginary zones A and B as indicated in FIGS. 3 and 4. The zone A may be associated with compression dies 20, 21, and the zone B or zones B may be associated with compression dies 30, 31. For example the zone A is preferably generally an area between the compression surfaces 20*a*, 21*a*, and the zone(s) B is preferably generally an area between the compression surfaces 30*a*, 31*a*. It is possible that during the compacting process ceramic particles change from zone A to zone B and/or vice versa, and it is also possible that the pressure applied to zone A will affect particles in zone B, and/or vice versa.

Figure 5:
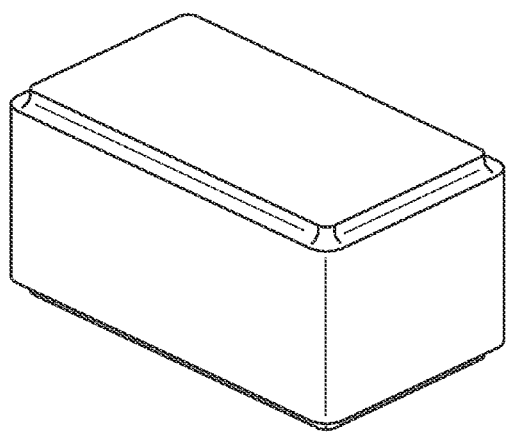
FIG. 5 is a three-dimensional view of a blank according to an embodiment of the invention.

According to a method of the invention the zones A, B may be compacted at pressures and/or positions that can be individually controlled, for example as illustrated in FIGS. 3 and 4. For example, the zone A may be compacted by moving the inner compression dies 20, 21 towards one another. Further, the zone(s) B may compacted by moving the outer compression dies 30, 31 towards one another. Therefore the zones A and B are generally independently compacted. It is to be noted that FIGS. 3 and 4 do not necessarily show a complete compaction cycle. In particular, FIG. 4 may not represent the status at the end of the compaction process, but at an intermediate point. In the example the opposing inner and outer compression dies start compacting the ceramic particles with the compression surfaces 20*a*, 30*a* of the lower compression dies 20, 30 positioned generally co-planar to one another, and with the compression surfaces 21*a*, 31*a* of the upper compression dies 21, 31 also positioned generally co-planar to one another (FIG. 3). In the following the lower and upper compression dies move towards another with the respective outer compression dies moving relative to the inner dies. In this case the outer compression dies move faster than the inner compression dies so that after a certain time the zone B is compacted at a greater compaction factor than the zone A as shown in FIG. 4. In case FIG. 4 shows the status at the end of the compaction process, a blank having a shape as illustrated in FIG. 5 may be obtained. Such blank may, for example, have overall dimensions of about 41×18.5×24 mm with a recess having dimensions of about 1.65×1.85 mm. However, it is also possible in the final state the respective compression surfaces of the inner and outer compression dies are again co-planar. In that case a generally cuboid blank may be created.

The following example describes in more detail the compaction process of the ceramic particles according to the method of the invention.

Figure 6:
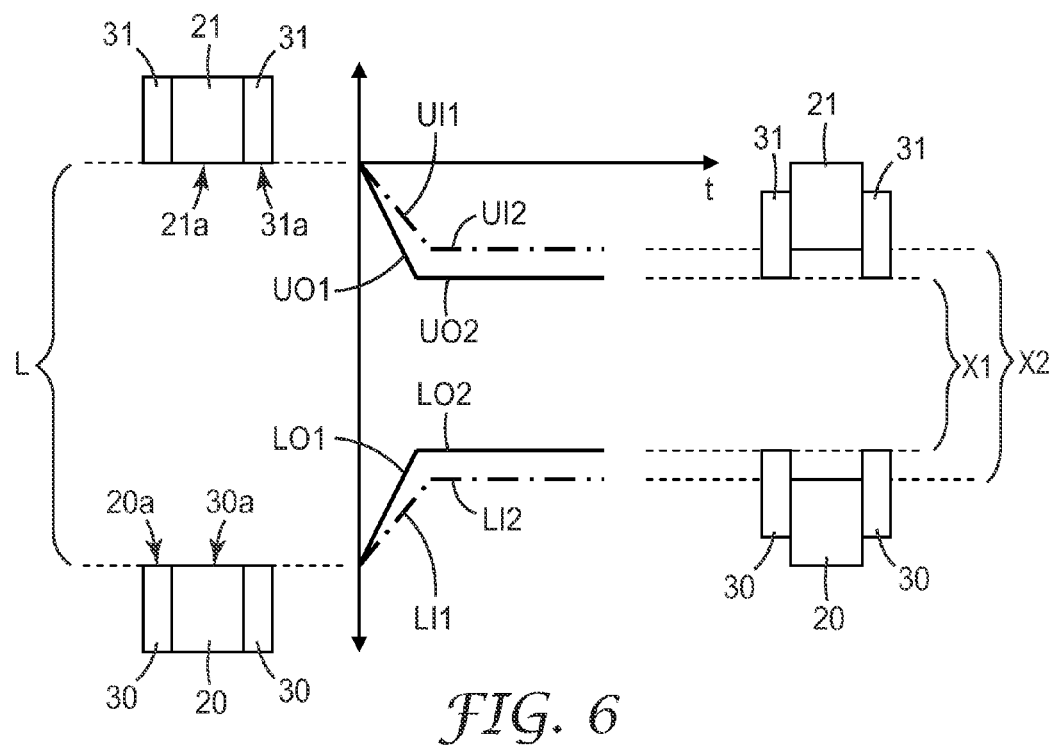
FIG. 6 is a diagram illustrating a compaction characteristic of a method according to an embodiment of the invention.

FIG. 6 shows a time (along the horizontal axis)-distance (along the vertical axis) diagram illustrating the position of the compression dies over time. On the left and the right of the diagram the initial and final position, respectively, of the compression dies 20, 21, 30, 31 are schematically outlined. In the initial state the upper compression dies 21, 31 are positioned with the compression surfaces 21a, 31a being co-planar. Also the lower compression dies 20, 30 are positioned with the compression surfaces 21a, 31a being co-planar. The curves LI and LO are associated with lower inner and outer compression dies 20 and 30 respectively, and curves UI and UO are associated with compression dies 21 and 31 respectively. In the compaction process shown the compression dies are moved position controlled (movement to a defined position, force may vary), and after a certain position is reached the compression dies are further moved force controlled (applying defined force, position may vary). In the example the control of position includes controlling the speed of the compression dies. By controlling the speed the quantity of ceramic particles may be first shaped to a certain desired preliminary shape. The majority of the compaction (biggest part of volume change) may be conducted by speed controlled movement of the compression dies. This may be advantageous to allow the ceramic particles to move relative to one another and thereby to maintain a rather uniform distribution of the ceramic particles at the stage of pre-shaping. And second, once the quantity of ceramic particles is pre-shaped, the compression dies may be moved at a controlled force. This may be advantageous to provide the quantity of ceramic particles with a desired density independently of tolerances of the initial quantity of the ceramic particles. At the stage of using force controlled compaction the volume of the quantity of ceramic particles may not change considerably. This also means that the compression dies may only make very short movements that may not be indicated in FIG. 6 and the following FIGS. 7 to 10.

From the initial state on the left of the diagram the compression dies are moved as represented by curve sections UI1, UO1, LI1, LO1. The curves UO1 and LO1 are steeper than curves UI1 and LI1 which indicates that the outer compression dies 30, 31 are moved at a higher speed than the inner compression dies 20, 21. All compression dies 20, 21, 30, 31 are stopped generally synchronously and held in position over some time as represented by curve sections UI2, UO2, LI2, LO2. Sustaining the position for a certain time period helps to achieve better homogeneity, for example. As mentioned, the compression dies may also be moved at a certain force within the curve sections UI2, UO2, LI2, LO2 (not shown). The compression dies may then be moved away from one another again, although this is not shown, thereby allowing the compacted blank to be removed from the tool.

Figure 7:
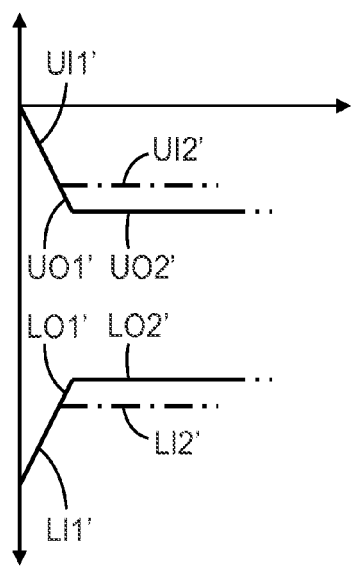
FIG. 7, 8 are diagrams illustrating with regard to FIG. 6 alternative compaction characteristics of a method according to embodiments of the invention.
Figure 8:
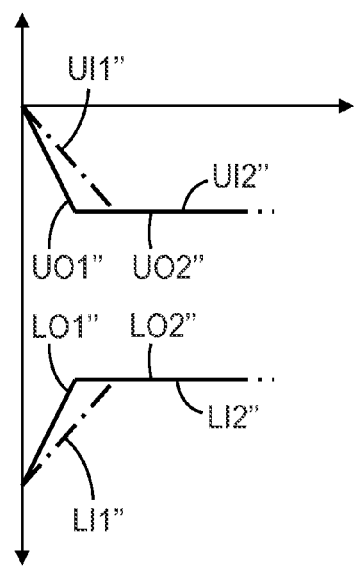
Figure 9:
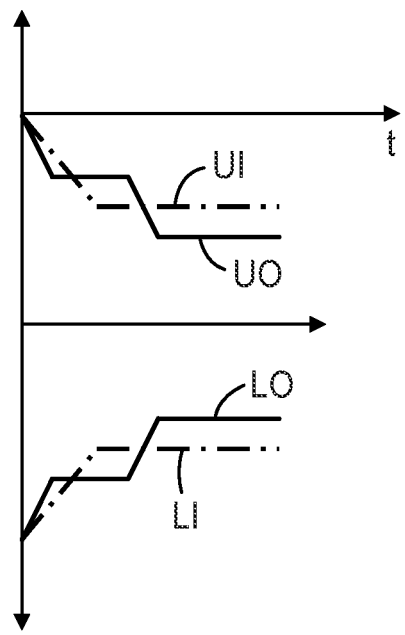
FIG. 9, 10 are diagrams illustrating further possible compaction characteristics of a method according to embodiments of the invention.
Figure 10:
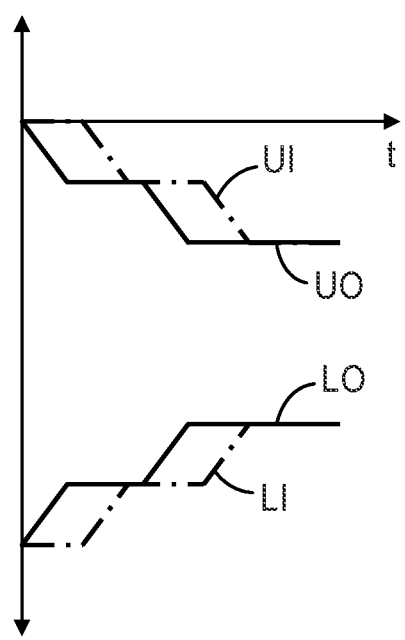

FIGS. 7 and 8 show alternative time-distance compaction profiles according to the invention. In FIG. 7 the inner and outer compression dies are moved at generally the same speed (UI1', UO1', LI1', LO1'), but the inner dies are stopped earlier than the outer compression dies. Therefore the inner and outer compression dies are in an offset position relative to one another as indicated by curve sections UI2', UO2', LI2', and LO2'. In FIG. 8 the inner and outer compression dies are moved at different speeds (UI1", UO1", LI1", LO1"), and the outer dies are stopped earlier than the outer compression dies. Therefore the inner and outer compression dies are in a generally aligned position (pressing surfaces co-planar) relative to one another as indicated by curve sections UI2", UO2", LI2", and LO2". There are many other modes possible, as for example, outlined by the diagrams of FIGS. 9 and 10. According to FIG. 9 the outer compression dies are moved stepwise (curves UO, LO), meaning that the outer compression dies are moved, held in position, and moved again. In contrast, the inner compression dies are only moved once and held in position (curves UI, LI). According to FIG. 10 the inner as well as the outer compression dies are moved stepwise. It is possible that a stepwise movement of the compression dies comprises more than one step. Further it is possible that any mode as described for the upper compression dies may be combined with any mode as described for the lower compression dies. In particular it is possible that either the upper or the lower compression dies are kept aligned with one another over the entire compaction process and the respective other compression dies are positioned offset relative to one another in at least one point in time during this process. It may also be possible to use a single compression die in cooperation with an inner and outer compression die, for example a single lower compression die and dual or multiple upper compression dies or the reverse. It is also possible to combine any of processes as outlined by example in FIGS. 6 to 10, for example in a way that the curves UI, UO of one example are combined with the curves LI, LO of any other example. For example, the upper outer compression dies may move fast and the lower outer compression dies move slowly with the lower inner and outer compression dies moving generally at the same speed.

Figure 11:
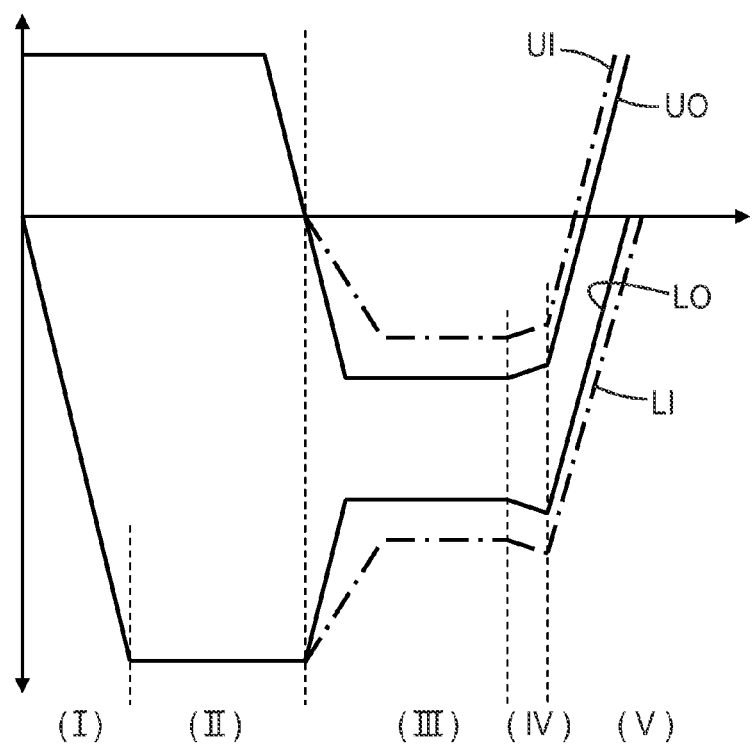
FIG. 11 is a diagram showing the curve of a compacting cycle according to an embodiment of the invention.

FIG. 11 shows a diagram which in contrast to the profiles previously shown in FIGS. 6 to 10 illustrates an extended compacting cycle how it may be used to make a blank according to the invention. The diagram includes additional strokes used for filling the chamber with powder, for ejecting the compressed blank, and other movements of the pressing dies that may be helpful in manufacturing a blank.

An exemplary material composition as it may be used with the present invention comprises:

Between 87% and 95% by weight zirconium oxide
Between 1%-5% by weight hafnium oxide
Between 0%-1% by weight aluminium oxide
Between 4%-6% by weight yttrium oxide The distribution of the particle size of the exemplary material composition may be:

10% of the particles smaller than 33 μm;
50% of the particles smaller than 65 μm; and
90% of the particles smaller than 100 μm.

Ceramic materials are for example available from the company Tosoh Corp. of Tokyo, Japan.

There are several sections in the profile of the diagram of FIG. 11 that represent movements and positions of the compression dies of a compression tool, for example one as described in FIGS. 3 and 4. At the start of the cycle (the left-most side of the profile), the lower inner and outer compression dies of the tool are initially positioned generally co-planar relative to one another, and flush with the upper end of the through-hole of the compression tool. The upper inner and outer compression dies of the tool are initially positioned outside the chamber of the tool and remote from the upper end of the through-hole. The press may be programmed to operate the compression dies of the tool according to the curves UI, UO, LI, LO. Each of the curves can be subdivided in several sections as designated with (I), (II), (III), (IV) and (V), which meanings are explained in the following by example only.

In step (I) both the lower inner compression die (curve LI) and the lower outer compression die (curve LO) are moved downwards to provide a chamber in the through-hole of the tool for filling with the ceramic particles. The stroke is determined so that the quantity of ceramic particles that could be received in the chamber is sufficient to form a blank of a desired size.

In step (II) ceramic particles are filled into the chamber provided in the tool. For filling the tool an automatic filling device may be used. The filling device may comprise a generally dome-shaped cap that can be positioned over the through-hole. The cap may be connected to a silo in which the ceramic particles may be stored. The ceramic particles may be fed from the silo into the cap and thereby into the through-hole so that the through-hole is preferably completely filled. The cap may be removed from the through-hole by sliding it sideways so that excess ceramic particles are wiped off by the cap. At this stage the ceramic particles may, for example, have a bulk density which is approximately between 1 g/cm$^3$ and 3 g/cm$^3$. The lower compression dies are typically not moved during this step. However, in the example the upper compression dies are moved on top of the ceramic particles to enclose the particles in through-hole of the tool (curves UI/UO).

In step (III) the ceramic particles are compacted by moving the upper and lower compression dies towards one another. The outer compression dies are moved at a higher speed than the inner compression dies (curve sections have different gradients). The speed of each of the inner dies may be approximately 10 mm per second to 20 mm per second, and in particular about 12.0 mm per second and the speed of each of the outer dies may be approximately 15 mm per second to 25 mm per second, and in particular 19.6 mm per second. Subsequently the compression dies are held in position with the compression surfaces of the inner and outer compression dies offset relative to one another.

In step (IV) a controlled relaxation of the compacted particles is allowed by moving the compression dies away from one another at a speed of approximately between 0.1 mm per second and 1 mm per second, and in particular at about 0.4 mm per second. Thus the compaction of the quantity of ceramic particles may be finished and the blank may be formed. The controlled relaxation may help avoiding the occurrence of cracks in the blank.

In step (V) the compression dies are repositioned in their initial positions. Thereby the lower compression dies may assist in the removal of the blank from the through-hole as indicated by the curve section terminating at the base line of the diagram.

The homogeneity of a blank as made by the method of the invention may be assessed by the following procedure. The blank may be sintered to the final density by exposing it to heat at temperatures of 1200° C. to 1650° C. for about 1 to 3 hours. At this stage the blank is typically generally free of air or voids, and therefore has a generally homogeneous density that substantially corresponds to the theoretical density of the ceramic material the ceramic particles are made of. A blank that initially has an inhomogeneous material structure will therefore generally shrink non-uniformly during sintering to arrive at the final density. As a result of a non-uniform shrinkage, the outer shape of the blank typically also changes non-uniformly, so that the final shape deviates from the exact proportions of the initial shape.

For assessing the initial homogeneity of a blank, a sample from the initial blank may be obtained and measured for reference. This sample is then sintered and the shape measured again. The sintered sample normally is smaller than the initial one, but non-uniform shrinkage can be determined based on distortions of the proportionally reduced shape relative to the initial or reference shape. Such distortions may then be used to draw conclusions regarding the homogeneity of the initial structure of the initial blank.

A sample may be obtained by first pre-sintering the initial blank as prepared in a compacting procedure, for example as described above. The sample may, for example, be pre-sintered by exposing the sample to heat at temperatures of between 850° C. to 1000° C. for a time period of between 0.5 and 4 hours. Pre-sintering is typically done to increase the mechanical stability of the blank, so that it can be handled more conveniently. From the pre-sintered blank a slice may be cut out, for example transverse to the length of the blank. Thus, a sample may be obtained that is relatively handy and fits with available measuring equipment. A cutting surface of the sample may then be polished so that the cutting surface becomes relatively planar. The planarity of the polished surface may be used as a reference surface and therefore may be measured for reference.

After sintering the reference surface of the sample may be measured again, and the measurements may be compared with the reference measurements. Inhomogeneities that may have been present in the sample in the pre-sintered stage may have caused distortions that can be detected in case the measurements before and after sintering deviate.

Figure 12:
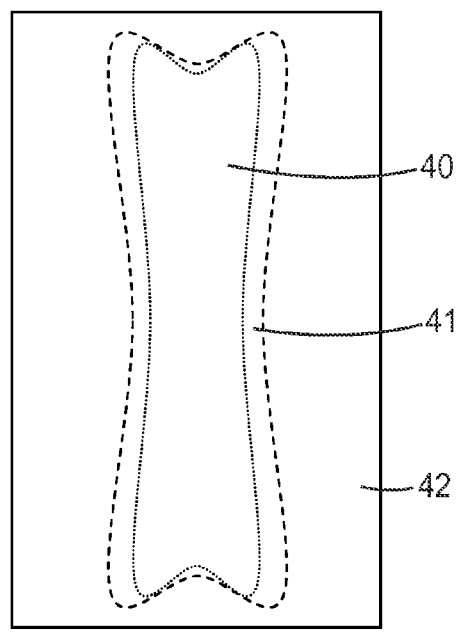
FIG. 12 is a schematic view of a homogeneity assessment that may be made using a blank according to an embodiment of the invention.

FIG. 12 schematically shows on a reference surface 42 areas 40, 41 of a blank having a relatively high density in its initial stage. Zones in a blank of a rather high density may also have a more homogeneous material structure or a more uniform density rather than zones having a lower density. Such level curves as shown may be obtained by measuring the reference surface at a plurality of locates distributed over the surface. An area of a relatively high initial density may be made physically visible on the reference surface in that the sample with its reference surface is rubbed on a generally planar metal surface. Raised areas resulting from a relative high initial density thereby touch the metal and obtain a dark silvery color, whereas deepened areas indicating a lower initial density maintain their natural color.

In FIG. 12 an area 40 is shown which may qualitatively represent an area of relatively homogeneous material structure as obtained from a blank according to prior art. In contrast area 41 may qualitatively represent an area of relatively homogeneous material structure as obtained from the invention. As illustrated the area 41 may be larger and therefore the blank obtained from the method of the invention may provide a larger usable area of the blank for making a dental restoration.

As mentioned the areas outlined in FIG. 12 are drawn qualitatively. In practice the areas generally do not have sharp boundaries, but more smoothly transit from darker colors to brighter colors. Further, the shapes may vary within certain a range.

The invention claimed is:

1. A method of making a dental blank from a quantity of ceramic particles, comprising the steps of:
    compacting a first zone of the quantity of ceramic particles;
    compacting a second zone of the quantity of ceramic particles;
    wherein the first and second zones have different compaction factors in at least one stage during compacting the first and second zones, and wherein the compaction of the first and second zones can be independently controlled.

2. The method claim 1, wherein the compaction factor of the first zone and the compaction factor of the second zone are in a ratio of between 0.8 and 2.0.

3. The method of claim 2, wherein the compaction factor of the first zone is greater than the compaction factor of the second zone.

4. The method of claim 1, wherein compacting the first zone is associated with moving a first movable member, and compacting the second zone is associated with moving a second movable member.

5. The method of claim 4, wherein compacting the first and second zones includes moving the first and second movable members, respectively, independently from one another.

6. The method of claim 4, wherein compacting the first and second zones includes moving the first and second movable members generally parallel to one another.

7. The method of claim 4, wherein the first and second movable members are moved relative to one another at a speed ratio of between 5:1 to 1:3.

8. The method of claim 4, wherein the first and second movable members shape first and second outer surfaces of the blank, respectively, wherein the first and the second outer surfaces form a generally co-planar outer blank surface.

9. The method of claim 4, wherein the first and second movable members shape first and second outer surfaces of the blank, respectively, wherein the first and the second outer surfaces are parallel and offset relative to one another.

10. The method of claim 1, further comprising the step of:
compacting a third zone of the body,
wherein the third zone and the second zone have different compaction factors in at least one stage during compacting the first, second and third zones.

11. The method of claim 10, wherein the compaction factors of the third and the first zones are generally the same.

12. The method of claim 10, wherein compacting the third zone is associated with moving a third movable member for compacting the third zone.

13. The method of claim 12, wherein compacting the first, second and third zones includes moving the first, second and third movable members in generally the same direction.

14. The method of claim 4, wherein compacting the first zone is further associated with moving a first pair of movable members, and compacting the second zone is associated with moving a second pair of movable members.

\* \* \* \* \*

UNITED STATES PATENT AND TRADEMARK OFFICE
CERTIFICATE OF CORRECTION

| | |
|---|---|
| PATENT NO. | : 8,425,812 B2 |
| APPLICATION NO. | : 12/682115 |
| DATED | : April 23, 2013 |
| INVENTOR(S) | : Ingo Wagner et al. |

It is certified that error appears in the above-identified patent and that said Letters Patent is hereby corrected as shown below:

In the Claims

Column 14,

Line 62, in Claim 2, after "method" insert -- of --, therefor.

Signed and Sealed this
Tenth Day of December, 2013

Margaret A. Focarino
*Commissioner for Patents of the United States Patent and Trademark Office*